(12) United States Patent
Guracar et al.

(10) Patent No.: US 7,004,906 B1
(45) Date of Patent: Feb. 28, 2006

(54) CONTRAST AGENT IMAGING WITH AGENT SPECIFIC ULTRASOUND DETECTION

(75) Inventors: Ismayil M. Guracar, Redwood City, CA (US); James E. Chomas, San Francisco, CA (US); Patrick J. Phillips, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 115 days.

(21) Appl. No.: 10/899,803

(22) Filed: Jul. 26, 2004

(51) Int. Cl.
*A61B 8/00* (2006.01)

(52) U.S. Cl. .................................. 600/447

(58) Field of Classification Search .............. 600/437, 600/443, 447, 454–458
See application file for complete search history.

(56) References Cited

U.S. PATENT DOCUMENTS

| | | | |
|---|---|---|---|
| 4,550,607 A | 11/1985 | Maslak et al. | |
| 4,699,009 A | 10/1987 | Maslak et al. | |
| 5,148,810 A | 9/1992 | Maslak et al. | |
| 5,261,408 A | 11/1993 | Maslak et al. | |
| 5,297,533 A | 3/1994 | Cook | |
| 5,410,208 A | 4/1995 | Walters et al. | |
| 5,415,175 A | 5/1995 | Hanafy et al. | |
| 5,438,998 A | 8/1995 | Hanafy | |
| 5,555,534 A | 9/1996 | Maslak et al. | |
| 5,562,096 A | 10/1996 | Hossack et al. | |
| 5,608,690 A | 3/1997 | Hossack et al. | |
| 5,657,295 A | 8/1997 | Howard et al. | |
| 5,670,746 A | 9/1997 | Hashimoto et al. | |
| 5,675,554 A | 10/1997 | Cole et al. | |
| 5,706,820 A | 1/1998 | Hossack et al. | |
| 5,757,727 A | 5/1998 | Hanafy et al. | |
| 5,792,058 A | 8/1998 | Lee et al. | |
| 5,916,169 A | 6/1999 | Hanafy et al. | |
| 5,920,523 A | 7/1999 | Hanafy et al. | |
| 6,177,923 B1 | 1/2001 | Arenson et al. | |
| 6,436,041 B1 * | 8/2002 | Phillips et al. | 600/437 |
| 6,494,841 B1 | 12/2002 | Thomas et al. | |
| 6,602,195 B1 * | 8/2003 | Krishnan et al. | 600/447 |
| 6,632,177 B1 | 10/2003 | Phillips et al. | |
| 6,638,228 B1 | 10/2003 | Brock-Fisher et al. | |
| 6,682,482 B1 | 1/2004 | Krishnan | |

* cited by examiner

Primary Examiner—Francis J. Jaworski (57) ABSTRACT

Highly specific measurements of flow in vessels, such as the coronary artery, can be obtained by processing cubic fundamental information. By showing flow in vessels with a high degree of contrast-to-tissue specificity, ultrasound based 3D contrast agent based coronary artery angiograms may be possible. Measurement and display of the velocity of agent from the cubic fundamental signal is provided simultaneously with display of cubic fundamental energy, such as providing a display map indexed by both energy and velocity. High pulse repetition frequency (PRF) for cubic fundamental detection in conjunction with long velocity measurement intervals may increase low velocity sensitivity and measurement precision. Pulsed wave (PW) Doppler may be improved by using a cubic fundamental sensitive pulse sequence. Using cubic fundamental sensitive techniques with other motion estimation techniques, such as two-dimensional velocity estimation or speckle tracking, may operate better than using other contrast agent detection techniques because of substantially reduced clutter.

17 Claims, 2 Drawing Sheets

CONTRAST AGENT IMAGING WITH AGENT SPECIFIC ULTRASOUND DETECTION

BACKGROUND

This present invention relates to contrast agent imaging. In particular, the cubic fundamental response provides agent specific ultrasound imaging.

Information at the cubic fundamental is detected by varying the transmit amplitude and phase associated with combined echo signals. Some techniques for detecting cubic fundamental information are disclosed in U.S. Pat. Nos. 6,494,841, 6,602,195, 6,632,177 and 6,682,482, the disclosures of which are incorporated herein by reference. The cubic fundamental information is highly specific to ultrasound contrast agents since contrast agents produce cubic response and the transducer and tissue produce very little cubic response. The information provides tissue clutter rejection, allowing for imaging more specific to contrast agents. For example, small vessels within tissue may be more easily imaged or identified using cubic fundamental information.

U.S. Pat. No. 6,638,228, the disclosure of which is incorporated herein by reference, provides for contrast-agent enhanced color-flow imaging. Power modulation or amplitude variation of the transmit pulses is used to obtain cubic fundamental information. A color Doppler estimator is used to detect the cubic fundamental information for imaging.

BRIEF SUMMARY

By way of introduction, the preferred embodiments described below include a method and systems for contrast agent imaging with ultrasound. Highly specific measurements of flow in vessels such as the coronary artery can be obtained by processing cubic fundamental information. By showing flow in vessels with a high degree of specificity, ultrasound based 3D contrast agent based coronary artery angiograms may be possible. The depiction of vessels in the liver, in particular their direction, is of great clinical interest during contrast agent exams. These and other applications may be available by improving flow estimation from or imaging of cubic fundamental information.

Different techniques for contrast agent imaging with cubic fundamental information are discussed herein. Measurement and display of the velocity of agent from the cubic fundamental signal is provided simultaneously with display of cubic fundamental energy, such as providing a display map indexed by both energy and velocity. High pulse repetition frequency (PRF) for cubic fundamental detection in conjunction with long velocity measurement intervals may increase low velocity sensitivity and measurement precision. Pulsed wave (PW) Doppler may be improved by using a cubic fundamental sensitive pulse sequence. Using cubic fundamental sensitive techniques with other motion estimation techniques, such as two-dimensional velocity estimation or speckle tracking, may operate better than using other contrast agent detection techniques because of substantially reduced clutter.

The techniques summarized above and/or disclosed below are used alone or in any possible combination. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Obtaining cubic fundamental information is disclosed in U.S. Pat. No. 6,494,841. Any of the transmit sequences and receive combinations disclosed therein may be used for obtaining cubic fundamental information for use with the flow imaging described below. Other transmit sequences and receive combinations for obtaining cubic fundamental information may be used, such as disclosed in U.S. Pat. Nos. 6,602,195, 6,632,177, 6,638,228 and 6,682,482. In general, a sequence of pulses with different amplitudes and phases are transmitted. Using amplitude change or different amplitudes without different phases may also be used to obtain cubic fundamental information. By combining received signals responsive to the sequence, a sample including cubic fundamental information is obtained. Velocity, energy or other flow parameters may be estimated from a plurality of the samples. The clutter or tissue rejection of the cubic fundamental information may be advantageously used in flow imaging of contrast agents.

Figure 1:
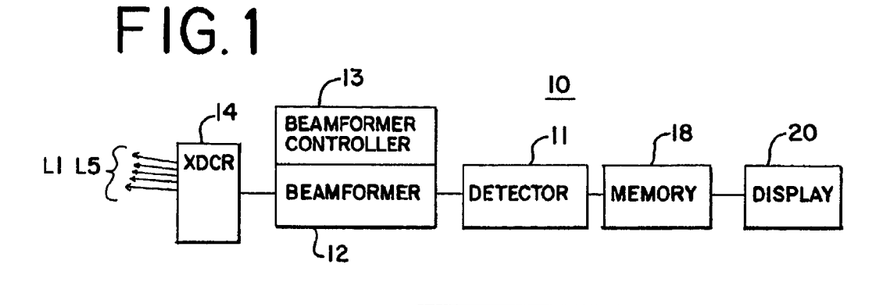
FIG. 1 is a block diagram of one embodiment of a system for contrast agent ultrasound imaging with cubic fundamental information.

FIG. 1 shows a system 10 for contrast agent imaging with ultrasound. The system 10 includes a beamformer 12, a beamformer controller 13, a transducer 14, a detector 16, a memory 18 and a display 20. Additional, different or fewer components may be provided, such as the system 10 without the memory 18 or with a scan converter or additional detectors. The system 10 is a medical diagnostic ultrasound imaging system in one embodiment, but other imaging systems of the same or different modality (ultrasound) may be used. The system 10 implements contrast pulse sequences (CPS) for obtaining information at the cubic fundamental.

The beamformer 12 is an ultrasound transmitter, transmit beamformer, receive beamformer, summer, filter, analog circuit, digital circuit or combinations thereof. The beamformer 12 is operable to obtain ultrasound data representing a cubic fundamental response. The beamformer 12 transmits a sequence of pulses associated with a given scan line, such as all the pulses along the line or the pulses along the scan line and adjacent scan lines. Responsive echoes are received. The beamformer 12 generates ultrasound data for each receive beam. By combining receive beams responsive to different ones of the pulses, cubic fundamental information is obtained.

The transmit sequence is controlled to generate echo signals responsive to the cubic fundamental. The beamformer 12 is operable to transmit a plurality of pulses having at least two different amplitude levels and at least two of the plurality of pulses having opposite phases. An ultrasonic transmitter that is coupled to the transducer 14 by a transmit/receive switch. The transmitter applies transmit signals of selected waveform timing and phasing to the individual elements of the transducer 14. In response, the transducer 14 creates ultrasonic pressure waves, which conventionally are focused along one or more scan lines L1, L2. In the conventional manner, scan lines L1, L2 are steered across the region of interest by properly adjusting the phase and time delays of the transmit waveforms. Scatterers in the region of interest return ultrasonic energy to the transducer 14, which in response forms echo signals that are applied by the transmit/receive switch to a receiver. The receiver applies appropriate phase and/or time delays to individual receive signals to cause the receive signals to add coherently from desired locations within the region of interest.

The transmitter, transducer 14 and receiver can take any desired forms. The widest variety of techniques can be used to implement the transmitter, including both analog and digital techniques. The following U.S. patents, all assigned to the assignee of the present invention, provide examples of the types and approaches that can be used to implement the transmitter: U.S. Pat. Nos. 4,550,607, 4,699,009, 5,148,810, 5,608,690, and 5,675,554. If desired, the transmitter may be used to form unfocused or only slightly focused pressure waves in the region of interest. These examples are of course not intended to be limiting in any way.

Similarly, the transducer 14 can take any desired form. The transducer 14 can be a 1-, 1.25-, 1.5-, 1.75- or 2-dimensional array of piezoelectric or capacitive membrane elements. By way of example, the transducers described in any of the following U.S. patents (all assigned to the assignee of the present invention) can readily be adapted for use with this invention: U.S. Pat. Nos. 5,261,408, 5,297,533, 5,410,208, 5,415,175, 5,438,998, 5,562,096, 5,657,295, 5,671,746, 5,706,820, 5,757,727, 5,792,058, 5,916,169, and 5,920,523. Once again, this list is not intended to be limiting, and any suitable transducer array can be used.

The receiver can include beamformers implemented using any suitable technology. For example, the beamformers described in the following U.S. patents (all assigned to the assignee of the present invention) can readily be adapted for use with this invention: U.S. Pat. Nos. 4,550,607, 4,699,009, and 5,555,534. Alternately, the receiver can include one or more beamformers that form beams on a point-by-point basis rather than a scan-line basis. As before, these examples are not intended to be limiting.

As described above, the amplitude and phase of transmitted signals are controlled to provide the desired contrast pulse sequence. In the system 10, the beamformer controller 13, such as a transmitter power and phase control, applies control signals to the beamformer 12 to create transmit pulses of the desired power and phase. Transmitter power can be varied in any suitable manner, as for example by adjusting the voltage applied to individual transducer elements, or by adjusting the number of transducer elements (or transmit aperture) used to form a particular pulse.

For obtaining ultrasound data at the cubic fundamental, the beamformer 12 includes line memories and a summer or a filter to combine signals responsive to the transmission of the CPS. Beamformed signals from the receiver are stored in the line memories or filter buffers. The line memories or buffers can be formed as physically separate memories, or alternately they can be formed as selected locations in a common physical device. The beamformed signals for a given CPS are stored in the line memories or buffers and then weighted and summed in a weighted summer. The weighted summer is controlled by the beamformer controller 13, such as a receive amplitude and phase weighting control, that provides the weighting values for both amplitude and phase that are used in the weighted summer. The memories and the summer can be implemented using analog or digital techniques. The weighted summer forms a composite output signal by weighting the separate beamformed receive signals in any of the ways described below. The composite output signal for a given spatial location is a sample associated with the cubic fundamental response.

In the foregoing example, the composite output signal was formed from a weighted summation of receive signals that had been beamformed. The weighted summation can be performed at baseband, IF or RF and prior to or after beamforming. Similarly, the weighted summation can be performed either before or after scan conversion.

The detector 16 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting information for display from beamformed ultrasound samples. In one embodiment, the detector 16 implements a fast Fourier transform from a plurality of samples representing a same region or gate location. Each of the samples is responsive to cubic fundamental so that a pulsed wave Doppler display may be generated from cubic fundamental information.

In another embodiment, the detector 16 is operable to estimate velocity, direction, and energy values as a function of the ultrasound data or samples. Two or more samples or combined signals responsive to the CPS pulses are input to the detector 16. The detector 16 determines the first and second coefficients of an auto-correlation function. The first order coefficient estimates energy, and the second order coefficient estimates velocity. Direction is derived from the velocity values by retaining the sign and removing the magnitude. Other calculations to estimate velocity and/or energy may be used, such as a cross-correlation or transform.

The memory 18 is a look-up table, buffer, random access memory, read only memory, combinations thereof or other now known or later developed device for storing data or a look-up table. The memory 18 is operable to store a display map. The display map may take many forms, such as separate display maps for either of energy or velocity. In one embodiment, the display map is indexed by both the velocity and energy values for outputting a display value. For example, the display map outputs a color value distinguishing between different energies or different velocities. A color value for one of the energy or velocity values for a spatial location is output as a function of the energy input. The color values representing velocity are displayed for higher energy, and the color values representing energy are displayed for lower energy. Color values representing energy are displayed for low velocity regardless of the energy level. The color values for energy are non-directional color coded, and the color values for velocity are directional color coded. Any threshold may be used for switching between the energy and velocity output values. In an alternative embodiment, a processor calculates the display values from one or more input sources of data.

The display 20 is a CRT, monitor, LCD, flat panel, projector or other display device. The display 20 receives display values for displaying an image. The display values are formatted as a one dimensional image, two dimensional image or a three dimensional representation. In one embodiment, the display values correspond to a PW Doppler image showing a range of frequencies modulated by energy as a function of time for one or more spatial locations. In another embodiment, the display values correspond to energy and/or velocity information for each spatial location. In yet other embodiments, B-mode, M-mode, velocity, energy, variance, contrast agent, harmonic or other types of images are displayed. The images are responsive, at least in part, to cubic fundamental information.

Figures 2, 3, 4:
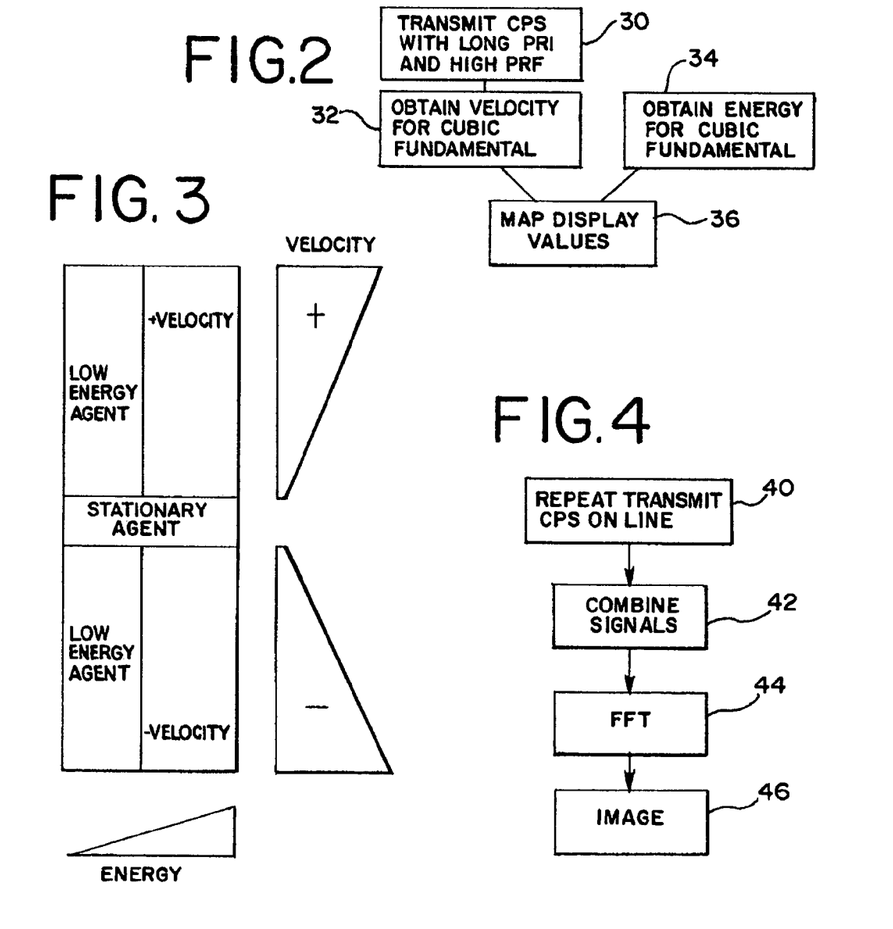
FIG. 2 is a flow chart diagram of one embodiment of a method for contrast agent ultrasound imaging with cubic fundamental information.
FIG. 3 is a graphic representation of a display map indexed by cubic fundamental based velocity and energy.
FIG. 4 is a flow chart diagram of another embodiment of a method for contrast agent ultrasound imaging with cubic fundamental information.

FIG. 2 shows one embodiment of a method for contrast agent imaging with ultrasound. Additional, different or fewer acts may be provided. For example, the acts of the methods of FIGS. 4 and/or 6 are performed along with the acts of FIG. 2. As another example, velocity estimates responsive to cubic fundamental transmissions are obtained in acts 30 and 32 without performing acts 34 and 36. As yet another example, cubic fundamental velocity estimates are obtained in act 32 without the long pulse repetition interval (PRI) and high sampling rate CPS pulses of act 30. The method of FIG. 2 is implemented using the system of FIG. 1 or another system.

In act 30, a sequence of pulses is transmitted (TX) for CPS. The sequence of pulses is transmitted along or adjacent to a scan line, L1. The sequence of pulses is used to form a plurality of samples for estimating velocity of contrast agent as a function of the cubic fundamental of the echo signals. The velocity is responsive to echoes from each of the pulses of the sequence.

Cubic fundamental signals can be obtained by transmitting an exemplary three pulses with varying amplitude and phase. A plurality of pulses having at least two different amplitude levels and at least two of the plurality of pulses having opposite phases are transmitted. For example, the sequence of pulses to obtain cubic fundamental information for a single sample for each depth location along a line is represented as [½ −1 ½]. The magnitude (i.e., ½ versus 1) represents amplitude and the polarity (i.e., negative versus positive) represents the relative phasing, here a 180 degree difference. [½ 1 ½] as well as other sequences with or without polarity changes or with different amplitude differences may also be used. It is preferred that the ½ amplitude pulses are achieved by using a subset of the full aperture, such as even or odd elements of the aperture, so may be represented as ½e for the even elements and ½o for the odd elements. Other aperture groupings to obtain the desired amplitude may be used.

A sample is formed by combining signals responsive to the transmitted pulses. In one embodiment, the signals for each pulse are equally weighted and summed, but unequal weighting with or without phase shifts may be performed for the combination of received signals. A sample is represented as $Y_N$. Each sample is formed from a unique combination. In one embodiment, the transmit pulses used for a given sample are used only for that sample. Alternatively, one or more pulses are used for different samples. Table 1 shows a contrast pulse transmit sequence along one scan line with receive filtering using shared pulses.

TABLE 1

| Transmit sequence | 1/2 e | −1 | 1/2 o | −1 | 1/2 e |
|---|---|---|---|---|---|
| Received point | $X_0$ | $X_1$ | $X_2$ | $X_3$ | $X_4$ |
| Receive weight $Y_0$ | 1 | 1 | 1 | | |
| Receive weight $Y_1$ | | 1 | 1 | 1 | |
| Receive weight $Y_2$ | | | 1 | 1 | 1 |

The $X_n$ corresponds to the order of transmission of the five pulses along the scan line. The "1" values are the weights applied to receive signals. The location of the "1" corresponds to the transmit pulses and associated received signals to be weighted. In table 1, three sets of samples $Y_0$, $Y_1$ and $Y_2$ for a same scan line are output.

The three samples are output from the filter block into the detector, such as a color Doppler autocorrelation detection processor. The velocity is estimated in act 32 as a function of the three samples or combined signals.

The $Y_1$ samples of Table 1 may have poor linear fundamental rejection, and may contaminate the detected agent energy and velocity estimates. The input receive signals may be reordered for input to a fixed clutter filter, and color Doppler detection performed with two desired points. Table 2 represents using the same transmit sequence, but reordering the resulting received signals for combination into two sets of samples.

TABLE 2

| Transmit sequence | 1/2 e | 1/2 o | −1 | −1 | 1/2 e |
|---|---|---|---|---|---|
| Received point | $X_0$ | $X_2$ | $X_3$ | $X_1$ | $X_4$ |
| Receive weight $Y_0$ | 1 | 1 | 0 | 1 | |
| Receive weight $Y_1$ | | 1 | 1 | 0 | 1 |

Alternative methods to discard or avoid the undesired output samples include decimation filtering and generalized matrix filtering. Other desired combinations responsive to cubic fundamental information input to the autocorrelation operation may be used.

There are many sequences that can be used to compute cubic fundamental sensitive contrast agent velocity. Additional points can be added to the sequences to improve the quality of the velocity estimates, such as shown in table 3.

TABLE 3

| Transmit sequence | | | | | | | Clutter filter | Est. samples | reorder pattern |
|---|---|---|---|---|---|---|---|---|---|
| 1/2 e | −1 | 1/2 o | −1 | 1/2 e | | | [1 0 1 1] | 2 | 0, 2, 3, 1, 4 |
| 1/2 e | −1 | 1/2 o | 1/2 e | −1 | 1/2 o | | [1 0 1 0 1] | 2 | 0, 2, 4, 1, 3, 5 |
| 1/2 e | −1 | 1/2 o | 1/2 e | −1 | 1/2 o 1/2 e −1 1/2 o | | [1 0 0 1 0 0 1] | 3 | 0, 3, 6, 1, 4, 7, 2, 5, 8 |
| 1/2 e | 1 | 1/2 o | 1 | 1/2 e | | | [−1 0 1 1] | 2 | 0, 2, 4, 1, 3 |

In table 3, the estimate samples represent the number of sets of combined signals or samples output for velocity estimation. The clutter filter represents the weighting for a moving window applied to the received signals of the CPS transmit pulses to obtain the samples. The reorder pattern is provided to present the desired data to the clutter filter for forming the samples. Other orders may be used.

Sequences may be adapted to provide improved sensitivity for low velocities in act 30. The pulses are spaced unequal distances apart in time within the sequence. For example, pulses for detection of cubic fundamental information are transmitted closer together in time than pulse sets for estimation of the velocity. Since different transmitted pulses are used for different samples, the sequence of pulses along a line or adjacent lines may provide pulses used for each sample at a high rate (i.e., relatively close spacing in time), but with the pulses different samples used for velocity estimation spaced apart in time.

In one embodiment, the spatial distribution of pulses of a sequence is obtained by interleaving pulses for other sequences. For example, pulses of a sequence used for forming samples on different, such as adjacent, scan lines are transmitted interleaved with pulses for a given scan line. The interleaving provides for a different number of pulses from other sequences being between two different sequential pairs of the pulses of a given sequence, resulting in variation of the time between pulses of the given sequence where a sequence is associated with pulses for two or more samples to be used for estimating a velocity.

In one embodiment for interleaving, equal spacing in time between the pulses is used. This interleaving is similar to interleaving for low velocity scale settings for conventional color Doppler. For example, if the flow sample interleave ratio (FSIR) is 3 (i.e., data for three spatially distinct scan lines are acquired in an interleaved fashion) and the sample count (i.e., number of pulses per scan line) is 6, then the total of 18 firings are acquired with the following ordering:

spatial line:

1 2 3 1 2 3 1 2 3 1 2 3 1 2 3 1 2 3

| -PRI- |

By convention, the PRI is defined as the time interval between pulses for the same spatial location. It corresponds to the velocity scale set by the user. A 6 pulse contrast pulse sequence with the same interleaving sequence showing the aperture weighting pattern is provided as:

$$1^{(1/2e)} 2^{(1/2e)} 3^{(1/2e)} 1^{(-1)} 2^{(-1)} 3^{(-1)} 1^{(1/2o)} 2^{(1/2o)} 3^{(1/2o)}$$
$$1^{(1/2e)} 2^{(1/2e)} 3^{(1/2e)} 1^{(-1)} 2^{(-1)} 3^{(-1)} 1^{(1/2o)} 2^{(1/2o)} 3^{(1/2o)}$$

The time between individual firings is PRI/3, or more generally PRI/FSIR.

By acquiring contrast pulse sequences with a long PRI, the velocity resolution for low velocities is increased. For example, the sample correlation is between complex clutter filter output samples that are 3*PRI apart in time. Sensitivity to linear fundamental clutter may be increased in the interleaving cases as well as the possibility of incoherence due to motion within the three pulses of the coherently combined CPS triplet (i.e., three pulses used to form one set of samples along a scan line) because of the longer PRI. To avoid this unwanted sensitivity, the pulses used for a given sample are maintained closer in time, providing unequal temporal spacing of pulses of the sequence. For example, at least six first pulses are transmitted. The six pulses correspond to two triplets or two sets of CPS pulses where each set has at least two pulses with different amplitude levels and at least two pulses with different phases. Three pulses (i.e., a first triplet) in the sequence corresponding to a first set of samples are transmitted free of interleaving. Pulses for one or more other sequences are than transmitted. Then, three more pulses (i.e., a second triplet) in the original sequence corresponding to a second set of samples are transmitted free of interleaving. This example sequence is represented by:

$$1^{(1/2e)} 1^{(-1)} 1^{(1/2o)} 2^{(1/2e)} 2^{(-1)} 2^{(1/2o)} 3^{(1/2e)} 3^{(-1)} 3^{(1/2o)} 1^{(1/2e)} 1^{(-1)} 1^{(1/2o)} 2^{(1/2e)} 2^{(-1)} 2^{(1/2o)} 3^{(1/2e)} 3^{(-1)} 3^{(1/2o)}$$

| ----- 3*PRI used for velocity estimate ----- |

This example sequence preserves high sampling rates for the CPS triplets while retaining the long correlation intervals for velocity sensitivity. Good linear fundamental clutter rejection is maintained because the second difference clutter filtering in this example is performed at a high sample rate (PRI/3). Increased velocity resolution is provided by the sample interleaving because the autocorrelation is performed across samples that are 3*PRI apart in time. Stationary and moving contrast agent may be better differentiated because of the greater velocity resolution.

In alternative embodiments, sets of four or more pulses are used instead of triplets (i.e., sets of three pulses) to acquire a given sample. In yet other embodiments, some interleaving is provided within the triplet or set of pulses for combination to obtain the cubic fundamental information. More or less relative interleaving is provided between the sets of pulses than shown in the example above or than used within the sets or triplets. In one embodiment, the pulses of a set used for obtaining cubic fundamental information are interleaved with another set in the same sequence. In yet another alternative embodiment, one or more pulses of a sequence are used for generating two or more samples.

Received signals responsive to each set of transmitted pulses are combined. The combination is performed as discussed above to obtain a sample or samples along a scan line responsive to cubic fundamental information. Received signals responsive to the different amplitude and phased pulses are combined to obtain cubic fundamental information. In the example above, received signals responsive to the first triplet (i.e., the first three pulses labeled "1") are combined, and the received signals responsive to the second triplet (i.e., the last three pulses labeled "1") are combined. By combining the received signals for each of the two or more sets of pulses in a sequence, two or more samples are generated for each given spatial location.

Velocities are estimated as a function of cubic fundamental signals responsive to the pulses of the sequence. The velocity at a given spatial location is estimated from the two or more samples formed from the sequence of transmit pulses. For example, a velocity is estimated from the two samples obtained using the "1" sequence transmit pulses in the example above.

In act 34, an energy of contrast agent is obtained. The energy is obtained as a function of a cubic fundamental of ultrasound signals. For example, a CPS sequence using all the same, all different or a sub-set of transmit pulses used to estimate velocity is transmitted. Using different pulses may result in received signals responsive to the same or different contrast agent due to movement of the contrast agent. A single sample or a plurality of samples is used to estimate the energy.

In act 36, an image is generated as a function of both the velocity and energy estimates. Calculations, processes or look-up table maps may be used for identifying display values for the image. The image is a black and white or color image. In one embodiment, a color map or look-up table indexed by the velocity and energy values is used to generate display values. FIG. 3 shows one such color map. One of the energy or velocity is displayed for a spatial location as a function of the energy. The velocity is displayed for higher energy, and the energy is displayed for lower energy. The velocity is a color, such as a directional color coded display value. For higher velocities, a different shade, brightness or hue is displayed. A different shade, brightness or hue is used to distinguish negative from positive velocities. For energies, a non-directional color coded display value is generated. The display values for energy are a different color, shade, hue or brightness than the display values for velocity. Low energy signals are shown without unreliable velocity estimates with a non-directional color coding. High energy signals with more reliable velocity estimates show a color-coded velocity.

The threshold or cut-off between displaying energy or velocity information is set by experimentation or in response to user input. In one region associated with stationary contrast agent, spatial locations associated with a sufficiently low velocity are displayed as black, as energy or as a non-velocity regardless of the energy level.

The map is used for each of a plurality of spatial locations to generate display values for a color image. The map can also be changed to show black (or the underlying tissue or B-mode in mix modes) in the locations where velocity is not mapped and/or stationary agent is located. The color mapping scheme then appears very much like a color Doppler map where stationary agent is suppressed. Alternatively, stationary agent is mapped to a color different from moving agent while the absence of agent is mapped to black or underlying B-mode. The map may be simplified to show only directional information rather than velocity. Any of the mapping or combinations shown in U.S. Pat. No. 6,177,923, the disclosure of which is incorporated herein by reference, can be applied here.

For imaging small vessels, signals associated with tissue velocity may be subtracted from velocities associated with both tissue and contrast agent velocities. Measurement of contrast agent flow velocities in vessels while inside moving tissue could allow vessels to be shown with high contrast despite the presence of perfused contrast agent in the tissues. Tissue velocity is determined using received signals without combination to find the cubic fundamental response. For example, tissue velocity is estimated from received signals for a sub-set of fewer than all of the pulses used in CPS. Using the 6-pulse sequence arranged as two identical 3 pulse triplets [½ −1 ½o] discussed above, the contrast and tissue agent velocity is provided by correlating across the triplets. The fundamental signal tissue velocity is obtained by correlating across the two full amplitude signals. In table 4 below, the complex filter output samples $Y_0$ and $Y_1$ yield the combined agent flow and tissue velocity measurement $V_{at}$. The samples $Z_0$ and $Z_1$ yield the tissue velocity measurement $V_t$.

TABLE 4

| Transmit sequence | ½ e | ½ e | −1 | −1 | ½ o | ½ o |
|---|---|---|---|---|---|---|
| Received point | $X_0$ | $X_3$ | $X_1$ | $X_4$ | $X_2$ | $X_5$ |
| Receive weight $Y_0$ | 1 | 0 | 1 | 0 | 1 | |
| Receive weight $Y_1$ | | 1 | 0 | 1 | 0 | 1 |
| Receive weight $Z_0$ | 0 | 0 | 1 | 0 | 0 | |
| Receive weight $Z_1$ | | 0 | 0 | 1 | 0 | 0 |

Alternatively, the tissue velocity is estimated from pulses not also used for estimating velocity.

The velocity estimates are obtained in parallel. Alternatively, one or more passes are performed through a same device to obtain the estimates sequentially from the same or different data.

To identify the velocity and contrast agents within a vessel, the tissue velocity is removed from the contrast agent and tissue velocity. The actual contrast agent flow velocity $V_a$ can be derived by subtracting the tissue velocity measurement $V_t$ from the combined agent and tissue velocity $V_{at}$. Alternatively, the input spectrum of the agent velocity measurement is modulated based on the tissue velocity measurement similar to adaptive clutter filtering. The tissue information is moved to 0, or zero velocity, so that the vessel contrast agent velocity remains. The information at and around 0 is then removed by clutter filtering.

The ½e and ½o pulses may also be used to help improve the quality of the tissue velocity estimate thru variance reduction, providing more averaged velocities. These pulses may have poor quality grating lobe performance where the reduction in amplitude is obtained by partially sampling the aperture. Combining these pulses coherently could improve grating lobe performance, but may introduce a zero in the amplitude frequency response of the tissue velocity estimator for high velocities.

Fundamental and/or second harmonic clutter velocity bias may be rejected by modulating the relative phases of the triplets or other groupings of pulses. The transmit phases are modulated to affect the velocity estimator to achieve improved velocity based detection specificity. Two sets of the contrast pulse sequence triplets [½e −1 ½o] provide a pair of complex values fed into the autocorrelators to generate a velocity estimate. Additional triplets can be used to increase the number of points that are averaged, reducing the variance of the velocity estimates. By altering the transmit phase of triplets in a particular sequence, the velocity estimates for linear fundamental, second harmonic, and cubic fundamental may be affected in useful ways.

The phase is altered between triplets or between combined triplets or other subset. Pulses of one sub-set of a sequence are transmitted with a different phase off-set than the pulses of another sub-set. The received signals responsive to each sub-set are combined to obtain information at the cubic fundamental. Each sample for velocity estimation corresponds to different sub-sets of pulses. The phase off-set is applied to different sub-sets of pulses. Where a pulse within a sub-set has a phase off-set relative to other pulses in the sub-set, the intra sub-set phase off-set is added to the sub-set phase off-set. The velocity is then estimated from the resulting samples.

For example, phase shifts are applied to a 9-pulse sequence containing three triplets. The phases applied to the three triplets are [0° 0° 90°]. A 90° phase shift is applied to each of the pulses in the third triplet and not to the pulses of the first two triplets. After combining the received signals for each triplet, three samples are input to estimate velocity. The first pair of complex samples fed to the autocorrelators has no relative phase change, so generate a normal velocity estimate. The second pair of samples has a positive 90° phase change for linear fundamental signals, 180° for second harmonic signals and a 270° or −90° phase change for cubic signals. When this second autocorrelation value or velocity estimate is averaged with the first, the true velocity from linear fundamental signals will see an average of a 45° positive bias. The measured velocity is higher by ¼ of the Nyquist velocity. The cubic fundamental has a bias of ¼ of the Nyquist velocity in the negative direction. The second harmonic has a zero bias, the first and second samples cancel each other out since they are of opposite phase. The velocity has zero bias due to second harmonic clutter.

In one embodiment, the second harmonic is reduced by filtering in CPS imaging so that there is less energy to affect cubic fundamental estimates. The filtering is performed by limiting axial bandwidth on receive, which affects range resolution. There is a tradeoff between second harmonic clutter and cubic fundamental bandwidth. In this phase off-set embodiment, by providing the relative phase off-sets, bias in the velocity estimate due to second harmonic signals is reduced when the axial bandwidth is broadened to include second harmonic signals.

More complete cancellation of information other than at the cubic fundamental is provided using a twelve pulse sequence with four triplets, each with transmit phasing of [0° 0° 120° 0°]. Three of the triplets are associated with a same phase off-set and a fourth one of the triplets has a different phase off-set. Samples are obtained for each of the triplets, such as each triplet including samples representing a same scan line. The velocity is estimated from the samples, such as from four samples for each spatial location. Using four samples, three complex correlated values are averaged by the autocorrelator. For fundamental frequencies, the velocities of the values to be averaged by the autocorrelators are shifted by [0° 120° −120°]. These sum to zero. The contribution of fundamental signal to the overall velocity estimate is nil or reduced. For the second harmonic, the shift is [0° 240° −240°]. These also sum to zero. The contribution of second harmonic signal to the velocity estimate is nil or reduced. For the cubic fundamental, the shift is [0° 360° −360°] which is equal to [0° 0° 0°]. These add constructively, resulting in a variance reduction benefit. The velocity estimate value for non-accelerating objects is mostly or entirely determined by the cubic fundamental signal. The velocity estimates from this four triplet twelve pulse technique help improve the specificity of agent flow in moving tissue. Only or mostly contrast agent signals produce a velocity estimate in non-accelerating moving tissue.

For the cases where large signals are from tissue (either harmonic or fundamental), the variance of the estimate may be used. For high energy cases where velocities cancel out, the variance estimate (1−abs(R(1)/R(0)) may be quite high since R(1) is zero where R(1) and R(0) are the autocorrelation coefficients. A large variance indicates clutter. The variance estimate is used to condition the display of low velocity signals with high energy. For example, one or both of the energy and velocity is not used or reduced for high variance conditions. This suppression may further remove signals from tissue.

Other sequences with phase off-sets using triplets or other groupings of CPS pulses may be used. For example, other phase sequences for a 3-triplet, 9-pulse sequence with transmit phase adjustments are possible. With a [0 45 0] phase adjustment, the two velocity estimate values each have a phase shift proportional to the harmonic order: [+45−45] fundamental (sums to zero bias), [+90−90] second harmonic (sums to zero complete rejection) and [+135−135] cubic (sums to a 180° bias). As another example in a [0 60 0] phase adjustment, the two velocity estimate values each have the following phase shifts: [+60−60] fundamental (sums to zero bias), [+120−120] second harmonic (sums to 180° bias) and [+180−180] cubic (sums to zero). This sequence rejects or reduces velocities from the cubic fundamental signal, so may be used to isolate parameters from the second harmonic signal.

In one embodiment of the CPS transmissions of act 30, the difference in amplitude of the transmitted pulses used to obtain information at the cubic fundamental is obtained by using different amplification or voltages. In other embodiments, the difference in amplitude is obtained by adjusting the aperture or number of elements and element spacing used for transmission of the pulses. For example, three or more sets of CPS pulses are transmitted in a sequence for a scan line. Each of the sets has a same amplitude and phase pattern of pulses. At least four of the pulses used in the sequence are responsive to a respective at least four different apertures. Other numbers of apertures may be provided. Three or more sets of received signals responsive to the three or more sets of transmitted pulses are combined respectively into three or more samples for velocity estimation.

For a simple example using the same three apertures for three sets of triplets in a sequence, higher order filtering may be used to increase the rejection of moving fundamental signals. The ½ −1 ½ set of pulses is arrived at by turning particular elements on and adjusting the polarity or phase of the transmitted waveform from each element as given below in table 5.

TABLE 5

| Full aperture | − | − | − | − | − | − | − | − |
|---|---|---|---|---|---|---|---|---|
| ½ aperture (even) | + | + |   |   | + | + |   |   |
| ½ aperture (odd) |   |   | + | + |   |   | + | + |

This aperture pattern has the desirable property that each element contributes an equal amount of positive and negative signal to the overall combined result. Each element within any of the apertures is used a same number of times as all of the other elements within any of apertures. This helps cancel certain system and transducer non-linearity. Alternatively, any given element may be used in different number of apertures for a sequence than another element. U.S. Pat. Nos. 6,602,195 and 6,682,482 disclose various aperture combinations for CPS pulses. The same or different apertures may be used for each set of pulses within a same sequence.

To achieve high order fundamental suppression and some cubic fundamental suppression, the following CPS set of [⅓ −1 1⅓] may be used. The following aperture function can be used to realize this set of pulses:

TABLE 6

| ¾ aperture (even) | − | − | − |   | − | − | − |
|---|---|---|---|---|---|---|---|
| ¾ aperture (odd) |   | + | + | + |   | + | + | + |
| ¼ aperture (odd) |   |   |   | − |   |   |   |
| ¼ aperture (even) | + |   |   | + |   |   |   |

Four different aperture patterns are used. An additional zero is provided at DC for linear fundamental suppression. A single zero cancels stationary cubic fundamental components. The specificity of moving agents detection may be improved.

In addition to the higher order aperture patterns discussed above, clutter filtering may be used to further enhance velocity estimation. For example, the adaptive clutter filter discussed above using long correlation intervals with high sampling rates is used in conjunction with the single cancellation zero available in the cubic fundamental signal space to more effectively separate moving agent from agent that is stationary relative to the moving tissue.

Longer CPS pulse sets may reduce sensitivity at low agent velocities. The previously discussed technique of rejecting the clutter bias might be a better way to make use of additional pulses to improve agent detection. This also has the variance reduction benefits to the velocity and energy estimates that come from averaging multiple autocorrelation samples.

A fourth order fundamental canceller of another embodiment using aperture weighting of amplitude has the following weights: [⅙ −⅔ 1 −⅔ ⅙]. The following aperture pattern can realize this by weighting the function [1 −4 6 −4 1]/8:

TABLE 7

| ¾ aperture | x | x | x |   | x | x | x |   | x | x | x |   | x | x | x |
|---|---|---|---|---|---|---|---|---|---|---|---|---|---|---|---|
| ½ aperture (even) | x | x |   |   | x | x |   |   | x | x |   |   | x | x |   |
| ½ aperture (odd) |   |   | x | x |   |   | x | x |   |   | x | x |   |   | x | x |
| ⅛ aperture (even) |   |   |   | x |   |   |   |   |   |   |   | x |   |   |   |
| ⅛ aperture (odd) |   |   |   |   |   |   |   | x |   |   |   |   |   |   |   | x |

Each "x" indicates the usage of a given element in a particular aperture. This five-pulse sequence has five different aperture amplitude functions. Each element contributes a single positive and single negative phase to the overall summation.

Crosstalk considerations may necessitate larger groupings of elements such that at least 2 or 4 adjacent elements are in use at all times (i.e., each "x" or column in Table 7 represents 2, 3, 4 or other number of adjacent elements). In higher order sequences four and five pulses can replace the triplets discussed earlier.

An alternative method for combining sequences to improve rejection is to apply not only different phases but vary transmit amplitude weights between triplets. Consider the following triplet: [½e −1 ½o]. For a 9 pulse sequence, three triplets with weights [½ 1 ½] are used. The actual transmitted aperture sequence is [¼ee ½e ¼eo ½e −1 ½o ¼oe −½o ¼oo] where "eo" or "oe" include even and odd elements or groups of elements. The aperture pattern for this sequence could be the following:

TABLE 8

| Full aperture | − | − | − | − | − | − | − | − |
|---|---|---|---|---|---|---|---|---|
| ½ aperture (even) | ± | ± |   |   | ± | ± |   |   |
| ½ aperture (odd) |   |   | ± | ± |   |   | ± | ± |
| ¼ aperture (even - even) | + |   |   |   | + |   |   |   |
| ¼ aperture (even - odd) |   | + |   |   |   | + |   |   |
| ¼ aperture (odd - even) |   |   | + |   |   |   | + |   |
| ¼ aperture (odd - odd) |   |   |   | + |   |   |   | + |

The apertures labeled with both "+" and "−" are used twice, once with positive phasing and once with negative phasing. This transmit sequence puts additional zeros at FS/2 and at FS/6 for increased fundamental cancellation. This could be helpful in very high clutter, shallow depth environments where the very low power signal of the ¼ aperture can penetrate, such as in transesophageal, intravascular applications or small animal imaging.

The triplet pattern is maintained so that within the group of 9 pulses, the values may be useful for other purposes. For example, the output of each triplet with appropriate receive weighting is obtained. Receive weighting is used since two of the three sets are associated with a half amplitude of the other set. A weight is applied to received signals or final samples of one, two or all three sets to equalize the amplitude contribution within the sequence. These resulting sample values are applied to the velocity estimator. The velocity estimate may be computed with normal levels of fundamental clutter rejection. The energy estimate may be computed with all 9 points with a higher level of fundamental clutter rejection and agent specificity. When these energy and velocity values are combined for display, such as with the map show in FIG. 3, the velocity is only displayed for signals with a high detected energy.

Contrast pulse sequence triplets or other sets of CPS pulses used in a sequence can be corrected by inserting a preamble pulse, represented as an initial additional pulse within the triplet: [½o ½e −1 ½o]. The amplitude and phase of the preamble or reverberation pulse is selected so that first three values sum to zero. This ensures cancellation of linear fundamental reverb signals. Techniques to determine the phase and amplitude of the reverberation suppression pulse are disclosed in U.S. Pat. No. 6,436,041, the disclosure of which is incorporated herein by reference. A second reverb pulse may be added as an initial negative one value: [−1 ½o ½e −1 ½o].

The reverb pulse or pulses generates a similar acoustic environment for each of the first pulses used in a combination to obtain a sample at the cubic fundamental. In an interleaving embodiment, each triplet (or other sub grouping) has a separate reverb firing. A 6-pulse sequence of two triplets without reverb cancellation uses an 8-pulse sequence for reverberation cancellation. For example, with a flow sample interleave ratio (FSIR) of four, 4×6=24 firings without reverb pulses has 4×8=32 firings with reverb pulses. Without a reverb pulse, the sequences for four lines are: 1 1 1 2 2 2 3 3 3 4 4 4 1 1 1 2 2 2 3 3 3 4 4 4. With the addition of one reverb firing per triplet, the sequences are: 1 1 1 1 2 2 2 2 3 3 3 3 4 4 4 4 1 1 1 1 2 2 2 2 3 3 3 3 4 4 4 4, where each triplet includes one initial reverb pulse. The superscripts denoting the aperture, phase and/or polarity function are omitted for clarity.

If there are not large phase changes between lines, then earlier triplets may serve as reverb pulses for subsequent triplets. A 9-pulse sequence may then become a 10-pulse sequence after a single reverb correction pulse is added to the beginning of the sequences. This assumes no phase changes between the groupings. If phase changes occur, then additional reverb pulses may be used. The time between firing each pulse is carefully controlled so that reverb pulses present the appropriate phase. In one embodiment, uniform pulse timing is used to control the phase.

One other way to reduce the number of reverb lines is by allowing some interleaving within triplets. For example, if the FSIR=4 with a two triplet six-pulse sequence, the following 24 firing pulses are provided: 1 2 1 2 1 2 3 4 3 4 3 4 1 2 1 2 1 2 3 4 3 4 3 4. Inserting single reverb pulses before each interleave triplet group provides 28 firings with the following sequences: 2 1 2 1 2 1 2 4 3 4 3 4 3 4 2 1 2 1 2 1 2 4 3 4 3 4 3 4. One reverb pulse for each interleaved triplet pair is provided, reducing the number of reverb pulses from the previous case by 50% (from 8 to 4). The contrast pulse sequence is acquired with a lower sampling rate (because of the interleaving) but a still longer correlation period. The lower sampling rate may introduce motion artifact due to imperfect cancellation of the fundamental signal.

The reverberation cancellation technique of using dead time before the triplet, i.e. [0 ½e −1 ½o], may be used. However, reflections from the first transmitted pulse from objects deep in the body may be seen when the second pulse is being received. Reflections from the second pulse may be seen on the third receive pulse. The first received pulse has no reflected signal. The three received pulses are combined with an FIR filter—in this case a [1 1 1 ] filter. The missing reflection on the first pulse may prevent cancellation of the linear fundamental signal from the deep objects. If the object is a bright reflector, such as the diaphragm, then the contrast agent detector will register a large signal. An example alternating polarity set of pulses without and with reverb pulses is provided as:

TABLE 9

| Tx Sequence: | 1/2 e | −1 | 1/2 o | |
|---|---|---|---|---|
| Reverb Signal: | | 1/2 e | −1 | |
| Rx weights: | 1 | 1 | 1 | → Reverb Sum: −1 + 1/2 e = −1/2 o |
| Tx Sequence | 1/2 o | 1/2 e | −1 | 1/2 o |
| Reverb Signal: | | 1/2 o | 1/2 e | −1 |
| Rx weights: | | 1 | 1 | 1 → Reverb Sum: −1 + 1/2 e + 1/2 o = 0 |

An example uniform polarity sequence without and with reverb pulses is provided as:

TABLE 10

| Tx Sequence: | 1/2 e | 1 | 1/2 o | |
|---|---|---|---|---|
| Reverb Signal: | | 1/2 e | 1 | |
| Rx weights: | 1 | −1 | 1 | → Reverb Sum: 1 − 1/2 e = 1/2 o |
| Tx Sequence | −1/2 o | 1/2 e | 1 | 1/2 o |
| Reverb Signal: | | −1/2 o | 1/2 e | 1 |
| Rx weights: | | 1 | −1 | 1 → Reverb Sum: 1 − 1/2 e − 1/2 o = 0 |

An alternative to reverb suppression pulses is to increase the time between firing each pulse with the commensurate tradeoff on linear fundamental clutter suppression and reduction in frame rate. The duration increase is between each of the firings.

The velocity scale may be adjusted to account for the sequences discussed herein with or without reverberation. Velocity estimates are obtained using one of different possible sequences of pulses corresponding different possible pulse repetition intervals. For example, the sequence is selected automatically in response to a type of examination or is selected as a function of user input. In response to the selection of a specific sequence and associated pulse repetition interval, a velocity scale annotation is adjusted as a function of the pulse repetition interval. One way to implement this could be to have a filter dependent scale factor for the velocity scale, such as a scale factor for multiplying the velocity scale used for annotation and calipers. The velocity scale is based on a particular PRI. By using the Doppler equation, Nyquist velocities are computed. For these various pulsing techniques, the velocity scale may have to be scaled (reduced) by integer factors which depend on the particular sequence. For example, the five pulse [½ −1 ½ −1 ½] set of CPS pulses has a true velocity scale which is one half as large. The six pulse set of CPS pulses is scaled by ½. Other sequences may require different scale factors.

In act 30, each of the pulses within a sequence is transmitted along a same scan line. Where interleaving between scan lines is used, the pulses of a plurality of sequences are transmitted along a respective plurality of scan lines. Table 11 below shows an acquisition pattern with three firings per detected line (i.e., set of CPS pulses for samples along a scan line). Linear fundamental suppression is provided by the second difference [1 −2 1] response. ultrasound line

TABLE 11

```
            ½e
            -1
        T   ½o
        i       ½e
        m       -1
        e       ½o
                    ½e
        ↓           -1
                    ½o
                        ½e
                        -1
                        ½o
            ┌────┬────┬────┬────┐
            │ L₀ │ L₁ │ L₂ │ L₃ │
            └────┴────┴────┴────┘
```

$L_n$ indicates the scan line.

In alternative embodiments, one or more pulses within a set of CPS pulses for forming samples along a scan line or within a sequence of multiple sets include at least one pulse transmitted along one line and another pulse transmitted along an adjacent line. For example, two pulses per detected scan line are used, resulting in linear fundamental suppression. Pulses are shared between scan lines or sequences. The lines are not collocated so there may be linear fundamental leakage. Phase correction and good sampling density may be used to improve linear fundamental cancellation. Table 12 shows this first alternative:

TABLE 12

| | | | |
|---|---|---|---|
| ½e | | | |
| -1 | | | |
| | ½o | | |
| | -1 | | |
| | | ½e | |
| | | -1 | |
| | | | ½o |
| | | | -1 |
| | | | ½e |
| L₀ | L₁ | L₂ | L₃ |

Some pulses are transmitted along scan lines located between the scan lines of interest.

In another alternative shown in table 13, only one pulse on average per detected line is used. Poor linear fundamental suppression may be provided. The second difference [1 –2 1] response is provided for lines $L_0$, $L_3$, $L_6$, etc., but the transmitted pulses within a set of pulses are not collocated, resulting in linear fundamental leakage. A linear fundamental suppression response for other lines ($L_1$, $L_2$, $L_4$, $L_5$, etc) may be worse than first difference performance [1 1 –2]. Line by line variation in linear fundamental suppression performance may produce artifacts in the final image. Lateral video filtering may help suppress the artifacts, trading off lateral resolution.

TABLE 13

| | | | | |
|---|---|---|---|---|
| ½e | | | | |
| -1 | | | | |
| ½o | | | | |
| ½e | | | | |
| | | -1 | | |
| | | ½o | | |
| | | ½e | | |
| | | | | -1 |
| | | | | ½o |
| L₀ | L₁/L₂ | L₃ | L₄/L₅ | L₆ |

Figure 5:
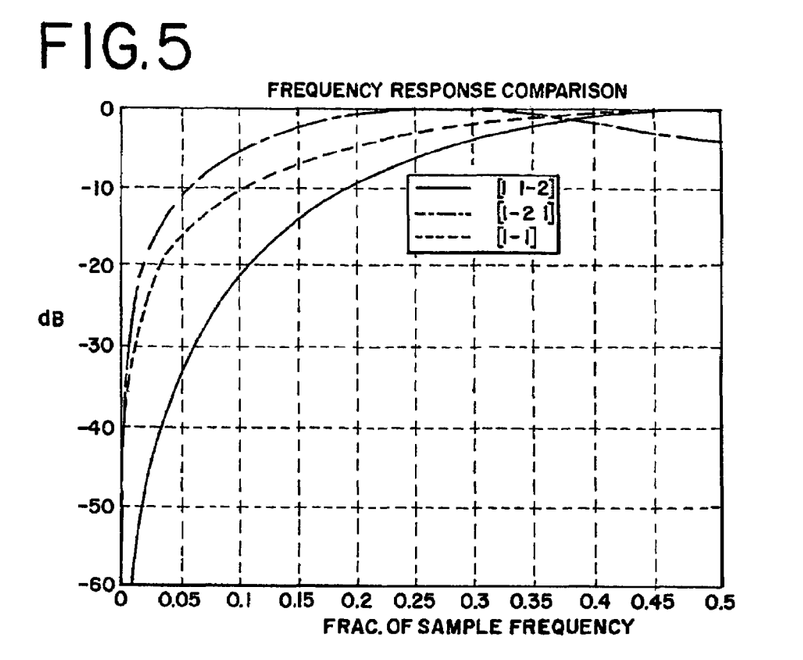
FIG. 5 is a frequency response plot of one embodiment of a contrast pulse sequence acquisition pattern.

The $L_1/L_2$ represents a scan line between $L_0$ and $L_3$. Samples are formed for each of $L_0$–$L_6$. FIG. 5 shows a frequency response of the linear fundamental suppression using the pulses of Table 13. The solid line represents the $L_1$ and $L_2$ response, the dot-dash line represents the $L_3$ response and the dotted line represents a first difference response for reference.

Table 14 represents yet another alternative transmit pattern. An average of 2 firings per detected line are used for linear fundamental suppression based on the second difference [1 –2 1] response. The scan lines are not collocated so there may be linear fundamental leakage.

TABLE 14

| | | | | | |
|---|---|---|---|---|---|
| ½e | | | | | |
| -1 | | | | | |
| | ½o | | | | |
| | -1 | | | | |
| | | ½e | | | |
| | | -1 | | | |
| | | | ½o | | |
| | | | -1 | | |
| | | | | ½e | |
| | | | | -1 | |
| | | | | | ½o |
| L₁ | L₂ | L₃ | L₄ | L₅ | L₆ |

Rather than estimating velocity or energy from samples representing the same spatial locations, the number of pulses may be decreased by estimating from adjacent spatial locations. Consider a CPS set of pulses where triplets are processed to produce linear fundamental suppressed complex values $Y_n$, such as shown in Table 15.

TABLE 15

| | | | |
|---|---|---|---|
| ½e | | | |
| -1 | | | |
| ½o | | | |
| | ½e | | |
| | -1 | | |
| | ½o | | |
| | | ½e | |
| | | -1 | |
| | | ½o | |
| | | | ½e |
| | | | -1 |
| | | | ½o |
| Y₀ | Y₁ | Y₂ | Y₃ |

The complex autocorrelation value for line n is represented as:

$R(1)_n = Y_n Y^*_{n-1}$ which correlates two complex values from different spatial scan lines. The velocity estimate for line n is then $<R(1)_n$. The velocity estimates may be obtained with only 3 pulses per line. Additional averaging could be performed:

$$R(1)^n = \sum_{k=n}^{n+1} Y_k Y^*_{k-1}$$

the spatial of the velocity estimate as well as adjust the spatial center of mass of the velocity estimates for these lines.

Other techniques may also be applied. For example, the transmit phases of consecutive triplets in adjacent lines can be modulated to help reduce the linear fundamental signal velocity bias. In one embodiment, twelve pulses of a sequence may be realized with a 9 pulses per scan line. Each entry in table 16 represents a 3-pulse CPS triplet acquired at a particular line Y.

TABLE 16

| | | | |
|---|---|---|---|
| 0° | | | |
| 0° | | | |
| 120° | | | |
| | 0° | | |
| | 0° | | |
| | 120° | | |
| | | 0° | |
| | | 0° | |
| | | 120° | |
| | | | 0° |
| | | | 0° |
| | | | 120° |
| $Y_0$ | $Y_1$ | $Y_2$ | $Y_3$ |

Three triplets acquired along a particular line ($Y_1$) are combined with a single triplet acquired from an adjacent line ($Y_2$) to form a single velocity estimate with reduced bias from linear fundamental and second harmonic clutter bias. The lines are close enough together to allow a reasonable velocity estimate to be made across lines, such as being adjacent scan lines.

The twelve pulse cancellation technique of the example embodiment above may be alternatively realized with an average of 1.5 triplets or 4.5 pulses per line. In the following table 17, each row represents collinear firings of the [½e −1 ½o] contrast pulse sequence *triplet*. E*ach* angle represents a transmit phase adjustment for all firings of a particular *triplet*.

TABLE 17

| | | | | | | | |
|---|---|---|---|---|---|---|---|
| 0° | | | | | | | |
| 120° | | | | | | | |
| | | 0° | | | | | |
| | | 0° | | | | | |
| | | 120° | | | | | |
| | | | | 0° | | | |
| | | | | 0° | | | |
| | | | | 120° | | | |
| | | | | | | 0° | |
| | | | | | | 0° | |
| $Y_0$ | $Y_1$ | $Y_2/Y_3$ | $Y_4$ | $Y_5/Y_6$ | $Y_7$ | $Y_8$ | |
| | $V_0$ | $V_1$ | $V_2$ | $V_3$ | $V_4$ | | |

The velocity values, V, are estimated based on the samples for each scan line, Y. For example, the velocities are estimated as $V_0 = <Y_1Y^*_0 + Y_2Y^*_1 + Y_3Y^*_2>$ and $V_1 = <Y_2Y^*_1 + Y_3Y^*_2 + Y_4Y^*_3>$.

FIG. 4 shows one embodiment of a flow chart diagram of another embodiment of a method for contrast agent ultrasound imaging with cubic fundamental information. Additional, different or fewer acts may be used, such as including any of the acts of FIG. 2 or related pulses, sets of pulses or sequences with or without interleaving. The method is implemented using the system of FIG. 1 or another system.

In act 40, a sequence of pulses is repetitively transmitted along a scan line. The sequence is free of interleaving in one embodiment. For example, the sequence is a set of pulses for obtaining one sample for each spatial location. By transmitting CPS pulses, the sequence corresponds to detection of cubic fundamental information. In one embodiment, the pulse sequence represented as ½e −1 ½o is repeated continuously.

In act 42, the received signals responsive to each repetition are combined. The combination of received signals corresponding to each set or sequence provides cubic fundamental information. The receive signals from each pulse of a triplet are added together in one embodiment.

In act 44, a fast Fourier transform (FFT) is performed as a function of the combined received signals from a plurality of the repetitions of transmission and combination. The samples are continuously fed into an FFT. The measurement PRI (the display velocity scale) is 3× the actual PRI. The two zeros may remove most of the linear fundamental clutter. Reverberation is handled naturally because each pulse of the sequence serves as natural reverb pulses for subsequent pulses. An initial reverberation pulse may or may not be used.

In act 46, an image responsive to the FFT is generated. The image is a pulsed wave (PW) Doppler image for a gate location along the scan line. Since the cubic fundamental information is used for the PW Doppler image, imaging flow in coronary arteries may benefit. The cubic fundamental information has high contrast agent specificity and low clutter. The lower clutter levels may also improve automated quantitative measurements.

In one embodiment, act 40 is performed using a high pulse repetition frequency (PRF). Sequential transmissions are performed with a lesser delay between transmissions. The delay may even be such that a second transmission is performed prior to an end of a time of flight for a location of interest for a first transmission. High PRF may provide good high velocity estimates with less concern for ghost gates being near strong clutter. Very low velocity scales may be used, and flows that would normally be obscured by clutter may be measured.

In some applications, such as coronary flow reserve studies, timing information is important. It is possible to create multiple Doppler strips. One strip is from data from the −1 transmit pulses and represents the fundamental signal energy containing significant tissue motion. Tissue motion provides heart cycle timing information (i.e. the start of systole and diastole). The other strip provides the cubic fundamental sensitive signal which is highly specific to the moving contrast agent. The two strips may also be stacked one on top of the other on the display or overlaid with different colors. The two strips may have the same or different effective measurement PRIs. The fundamental pulses may be sub-sampled to get a PRI that is an integer multiple longer for the fundamental strip than for the cubic fundamental strip. The receive weights and phases may be altered from the ½e and ½o pulses so that all pulses can be used for a fundamental sensitive strip and a shorter measurement PRI can be used. Since tissue timing information is of interest, clutter leakage from imperfect cancellation may be less of a concern.

Cubic fundamental velocity, energy, intensity and/or other type of information is used for three-dimensional imaging in one embodiment. To reduce scan time or frame rate, different pulses are transmitted along different lines in a volume. The CPS pulses to form samples along a scan line are transmitted along a same or different scan lines. Table 18 shows a 2 dimensional sampling pattern of CPS triplets acquired in order from 1–16 for a total of 16×3 =48 line firings:

TABLE 18

| 1 | 3 | 5 | 7 | 9 | 11 | 13 | 15 |
|---|---|---|---|---|----|----|----|
| 2 | 4 | 6 | 8 | 10 | 12 | 14 | 16 |

In one embodiment, these triplets are acquired with the transmit phase angles shown in table 19:

TABLE 19

| 0 | 120 | 0 | 0 | 120 | 0 | 0 | 120 |
|---|-----|---|---|-----|---|---|-----|
| 0 | 0 | 120 | 0 | 0 | 120 | 0 | 0 |

The velocity estimates are formed with samples for 4 triplets of 7 scan lines centered at each group of four. Groups of 4 lines are combined in one embodiment as shown in Table 20.

TABLE 20

| Line combination | phase sequence |
|---|---|
| 1, 2, 3, 4 | 0, 0, 120, 0 |
| 3, 4, 5, 6 | 120, 0, 0, 120 |
| 5, 6, 7, 8 | 0, 120, 0, 0 |
| 7, 8, 9, 10 | 0, 0, 120, 0 |
| 9, 10, 11, 12 | 120, 0, 0, 120 |
| 11, 12, 13, 14 | 0, 120, 0, 0 |
| 13, 14, 15, 16 | 0, 0, 120, 0 |

These phase sequences have 0, +120 and −120 degree phase differences in different orders. The phase differences produce fundamental clutter velocity bias cancellation. The average number of pulses to acquire these 7 scan lines is 48÷7≈6.9 firings.

The energy estimates are formed with a higher spatial sampling density than the velocity estimates. Each energy estimate may be formed from a single set of pulses, resulting in a greater sampling density. Spatial filtering operations to smooth out artifacts can be set to account for the different parameter sampling densities. For example, the spatial smoothing coefficients are varied to increase the amount of smoothing of the higher density energy estimates to reduce speckle and reduce the amount of smoothing of the lower density velocity estimates. The smoothing equalizes the actual resolution after reconstruction between the velocity and energy estimates.

A three-dimensional image is generated as a function of the cubic fundamental transmissions and received signal combinations. Any detected data may be used for generating the image. Where both velocity and energy estimates are used, the different in sampling grid is accounted for in scan conversion and/or in the 3D reconstruction.

Volume flow measurements before and after drug or exercise challenges are useful in clinical determinations of heart health. Cross sectional area measurements in 2D images are problematic due to unknown vessel orientation. Clutter is also a serious limitation to mean velocity computation. In practice, the maximum velocity waveform is used and relative measurements are made before and after cardiac challenge to derive coronary flow reserve. Contrast agent flow in coronary arteries in 3D is shown with a high degree of specificity to actual blood flow by the cubic fundamental information (rejecting fundamental clutter). Vessel cross sectional area measurements (derived from the cubic fundamental 3D vessel image) may be combined with mean velocity information (again derived from the cubic fundamental signals from moving agent) to compute volume flow. Volume flow changes before and after challenge may be clinically useful. Since there are small variations in the size of the coronary artery before and after challenges, it may be sufficient to use the time integrated mean velocity waveform in clinical comparisons. This may provide better accuracy over the maximum velocity waveform. The rejection of tissue clutter provided by the cubic fundamental agent information enables the mean waveform to be used.

Figure 6:
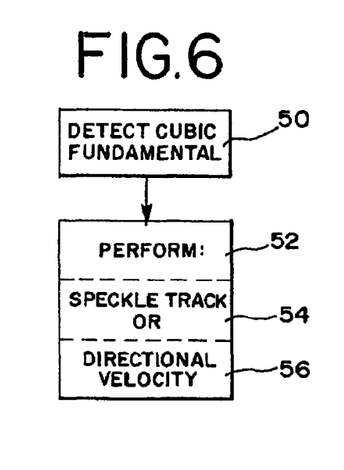
FIG. 6 is a flow chart diagram of yet another embodiment of a method for contrast agent ultrasound imaging with cubic fundamental information.

FIG. 6 shows another embodiment of a method for contrast agent ultrasound imaging with cubic fundamental information. Additional, different or fewer acts may be used, such as including any of the acts of FIG. 2 or 4 or related pulses, sets of pulses or sequences with or without interleaving. The method is implemented using the system of FIG. 1 or another system.

In act 50, cubic fundamental information is detected. Any of the CPS techniques discussed above may be used. The detected data may include only cubic fundamental information or information in addition to the cubic fundamental. The detected cubic fundamental information is detected at one or more spatial locations, such as along two intersecting lines or for each of a plurality of locations in a region at two different times.

In act 52, one or more motion estimation techniques are performed. For example, one or both of acts 54 and 56 are performed. Acts 54 and 56 correspond to obtaining directional velocity information, either of one frame of data relative to another frame of data or of a multi-dimensional velocity vector for a given spatial location. Other motion estimation techniques different than one dimensional velocity or energy detection may be used. The techniques take advantage of the clutter rejection and/or other characteristics of the cubic fundamental information. The linear fundamental clutter rejection available from the CPS triplet and the specificity to cubic fundamental signals allows a number of motion estimation techniques to be more likely to succeed. For example, the techniques of spatial quadrature, cross correlation, and speckle tracking all have serious limitations due to clutter. Operating these techniques on clutter free cubic fundamental signals allow more practical use of these techniques. Lateral velocity estimation may be more accurate without clutter. Low velocity information without clutter by detecting the cubic fundamental may be possible without frame rate reduction due to large clutter filters.

Figure 7:
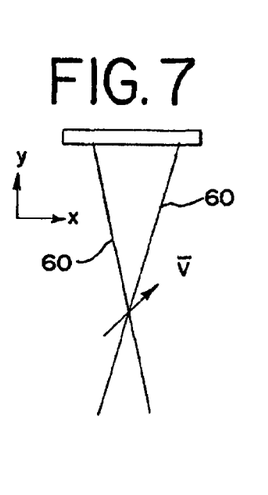
FIG. 7 is a graphical representation of a cross beam method for determining a two-dimensional velocity.

In act 56, a directional velocity estimate is obtained. For example, a two or three-dimensional velocity is obtained. In one embodiment represented in FIG. 7, cubic fundamental information is obtained along two intersecting scan lines 60. Velocity estimates at the point of intersection provide velocity information in each of the two different scan line directions. The geometric relationship of the scan lines may be used to determine a two-dimensional velocity. For cross-beam detection methods low lateral spatial-frequencies/velocities remain and vector estimates become more accurate, especially for velocities predominantly in the x-direction. A three dimensional velocity vector may be derived from three intersecting beams or the tracking of speckle between two acquired volumes with the use of a 2D transducer array. A 3D velocity vector may also be derived from two separate two-dimensional velocity vectors from orthogonal planes within a volume.

Figure 8:
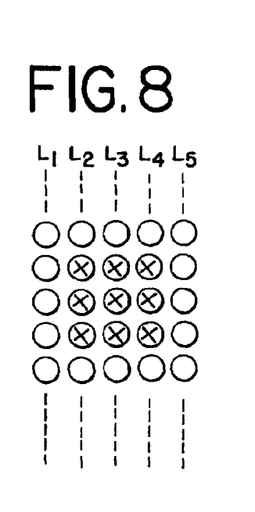
FIG. 8 is a graphical representation of a speckle search method.

In act 54, speckle tracking is performed. FIG. 8 shows speckle tracking between the two different times where "X" indicates data from one frame of data and "O" indicates data from a different frame of data. The spatial locations marked "X" are a region of interest or speckle information to be tracked. By tracking the region from one frame to another frame, the relative motion of the region is determined. Before tracking the velocity using the target region within a search region (e.g., locations labeled with "O"), clutter is removed. A flow sample count (i.e., the number of firings to a same location) number of pulses are acquired per line $L_i$ (i=1, 5). By using cubic fundamental information, a simple or no clutter filter may be used to remove clutter information. Correlation, sum of absolute differences or other calculation is used to determine a sufficient match of translation and/or rotation of the target region to the search region.

Before tracking the velocity using the target region within a search region, clutter is removed. Pulses are acquired per line $L_i$ (i=1, 5) and filtered with T taps/coefficients of the clutter filter. For low velocity detection, a clutter filter with more than three coefficients is used so the transition band between the stop band and the pass band is narrow and strong clutter signals may not override the weaker blood signals. Using the following 'minimal' example with a flow sample count of 4 (FSC=4) and T=4, the frame rate is primarily determined by transmitting (4×5)+(4×3)=32 pulses. If the pulses where acquired sequentially in space across lines $L_i$ and then repeated to build up the FSC number of pulses per line, the number of filter coefficients is greater than 4 for the same minimum detectable velocity since more time exists between pulses filtered by the clutter filter. This latter alternative reduces frame rates even further. For speckle-tracking methods, low lateral velocities also remain and in addition less transmit pulses are required. Since only a minimum of three pulses are required per line in each of the target and search regions, the total number of pulses in the example above drops to (3×5)+(3×3)=24 instead of the 32 pulses. For detecting even lower velocities, the improvement in frame rate may be greater given the need for a larger number of clutter filter coefficients and therefore more transmit pulses beyond 4 per line.

For each line in the cross-beam, speckle-tracking, or other method of detecting vector motion, N pulses are fired as fast as practical and combined appropriately to suppress linear fundamental energy and detect cubic fundamental. This step for each line effectively eliminates or reduces clutter, leaving nonlinear energy to be used for detecting stationary, slowly, or quickly moving blood or contrast agent. Since this step effectively separates clutter (at linear fundamental frequency) from the desired blood flow (at nonlinear fundamental), movement over a range of velocities can be detected and any significant biases may be minimized.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for contrast agent imaging with ultrasound, the method comprising:
   (a) transmitting a first sequence of first pulses along or adjacent to a first line, the first pulses having an unequal distance apart in time within the sequence; and
   (b) estimating a first velocity as a function of cubic fundamental signals responsive to the first pulses of the first sequence.

2. The method of claim 1 further comprising:
   (c) transmitting second pulses of one or more other sequences along one or more lines different than the first line, the transmission of the second pulses interleaved with the transmission of the first pulses, a different number of second pulses being between two different sequential pairs of the first pulses.

3. The method of claim 1 wherein (a) comprises transmitting at least six first pulses wherein at least two of the first pulses have different amplitude levels within the first sequence;
   further comprising:
   (c) combining first and second sets of received signals responsive to the transmission of (a) and first and second different sets, respectively, of the first pulses into at least two samples; and
   wherein (b) comprises estimating the first velocity from the at least two samples.

4. The method of claim 3 wherein (c) comprises combining for each of the at least two samples received signals responsive to the different amplitude levels.

5. The method of claim 3 wherein (a) comprises:
   (a1) transmitting at least three first pulses free of interleaving;
   (a2) transmitting second pulses of one or more different sequences; and then
   (a3) transmitting at least three first pulses free of interleaving;
   wherein (c) comprises:
   (c1) combining received signals responsive to the transmission of (a1) for a first of the at least two samples; and
   (c2) combining received signals responsive to the transmission of (a3) for a second of the at least two samples; and
   wherein (b) comprises estimating the first velocity from the first and second samples.

6. The method of claim 1 wherein (a) comprises transmitting first pulses for detection of cubic fundamental information closer together in time than first pulses for estimation of the first velocity.

7. The method of claim 1 further comprising:
   (c) estimating tissue velocity from a sub-set of fewer than all of the first pulses; and
   (d) removing the tissue velocity from the first velocity.

8. The method of claim 1 further comprising:
   (c) obtaining at least first and second samples responsive to first and second sub-sets of the first pulses, respectively, the first sub-set different than the second sub-set;
   wherein (a) comprises transmitting the first pulses of the first sub-set with a different phase off-set than the first pulses of the second sub-set; and
   wherein (b) comprises estimating the first velocity from the first and second samples.

9. The method of claim 8 wherein (a) comprises transmitting four different triplets of first pulses, three of the triplets associated with a same phase off-set and a fourth one of the triplets having a different phase off-set, wherein (c) comprises obtaining four samples each responsive to a respective triplet, and wherein (b) comprises estimating the first velocity from the four samples.

10. The method of claim 1 wherein (a) comprises transmitting the first pulses wherein at least two of the first pulses have different amplitude levels within the first sequence, the different amplitude levels responsive to different apertures.

11. The method of claim 10 wherein (a) comprises transmitting at least three sets of first pulses, each of the at least three sets having a same amplitude pattern of first pulses, at least four of the first pulses responsive to a respective at least four different apertures, each element within any of the at least four apertures being used a same number of time as all of the elements within any of the at least four apertures;

further comprising:
(c) combining at least three sets of received signals responsive to the at least three sets of first pulses, respectively, into at least three samples; and wherein (b) comprises estimating the first velocity from the at least three samples.

12. The method of claim 1 further comprising:
(c) transmitting a reverberation pulse corresponding to generating a similar acoustic environment for each of the first pulses used in a combination to obtain a sample at the cubic fundamental.

13. The method of claim 1 wherein (a) comprises transmitting all the first pulses along the first line.

14. The method of claim 1 wherein (a) comprises transmitting at least two sets of first pulses, each of the sets of first pulses including one first pulse along the first line and another first pulse along an adjacent line.

15. The method of claim 1 wherein (a) comprises transmitting different first pulses along different lines in a volume;

further comprising:
(c) generating a three-dimensional image as a function of the transmissions of (a).

16. The method of claim 1 wherein (a) comprises obtaining the first velocity using one of different possible sequences of first pulses corresponding different possible pulse repetition intervals;

further comprising:
(d) adjusting a velocity scale annotation as a function of the pulse repetition interval of the used one of the different possible sequences.

17. The method of claim 1 wherein (b) comprises obtaining the first velocity as one of: a two-dimensional velocity vector or a three-dimensional velocity vector.

* * * * *